United States Patent
Pappou (12) United States Patent (10) Patent No.: US 10,555,816 B1
(45) Date of Patent: Feb. 11, 2020

(54) SYSTEMS AND METHODS OF A GLENOID COMPONENT

(71) Applicant: Shoulder Innovations, LLC, Palm Harbor, FL (US)

(72) Inventor: Ioannis P. Pappou, Palm Harbor, FL (US)

(73) Assignee: Shoulder Innovations, LLC, Palm Harbor, FL (US)

(*) Notice: Subject to any disclaimer, the term of this patent is extended or adjusted under 35 U.S.C. 154(b) by 0 days.

(21) Appl. No.: 16/273,470

(22) Filed: Feb. 12, 2019

(51) Int. Cl.
*A61F 2/40* (2006.01)
*A61F 2/30* (2006.01)
*A61F 2/46* (2006.01)

(52) U.S. Cl.
CPC ........ *A61F 2/4081* (2013.01); *A61F 2/30771* (2013.01); *A61F 2/30734* (2013.01); *A61F 2/4612* (2013.01); *A61F 2002/4085* (2013.01)

(58) Field of Classification Search
CPC combination set(s) only.
See application file for complete search history.

(56) References Cited

U.S. PATENT DOCUMENTS 8,840,668 B1 * 9/2014 Donahoe ............ A61B 17/1604
623/17.16

* cited by examiner

*Primary Examiner* — Yashita Sharma
(74) *Attorney, Agent, or Firm* — Foley & Lardner LLP; Shabbi S. Khan (57) ABSTRACT

A glenoid component includes a body, a first, convex surface, a second, concave surface, a third surface connecting the first and second surfaces, a channel, and at least one alignment member. The channel extends from a first channel opening of the first surface through the body to a second channel opening defined on the third surface and has a channel axis extending through the first and second channel openings. The channel axis intersects a first plane defined by the first channel opening at an angle transverse to the first plane. The channel is configured to receive a bone engagement member to attach the body to a shoulder bone. The at least one alignment member extends from the first surface to align the body to the shoulder bone. The bone engagement member can attach the body to the shoulder bone.

19 Claims, 9 Drawing Sheets

SYSTEMS AND METHODS OF A GLENOID COMPONENT

TECHNICAL FIELD

The present disclosure generally relates to the field of shoulder replacement surgery, and more specifically to systems and methods of all-metal glenoid components.

BACKGROUND

Total shoulder arthroplasty (TSA), a type of shoulder replacement surgery, is performed to repair a patient's shoulder joint, such as when joints have been damaged or lose functionality due to disease, bone loss, or arthritis. Glenohumeral arthritis can occur in the posterior part of the shoulder joint and can erode the glenoid eccentrically. In some cases, the humeral head becomes decentered and erodes the posterior part of the shoulder joint, making it difficult to anchor a glenoid component to the shoulder bone. A glenoid component, such as a plastic augmented glenoid component, may be cemented to the shoulder bone, and a bone graft may be used to address the problem of bone loss. However, even with a bone graft, posterior bone erosion can occur even after a total shoulder arthroplasty, which may cause additional problems and reduce the effectiveness of a total shoulder arthroplasty.

SUMMARY

According to an aspect of the present disclosure, the glenoid component includes a body, a first surface, a second surface, a third surface, a channel, at least one alignment member and a bone engagement member. The first surface has a convex shape. The second surface has a concave shape and is opposite the first surface. The third surface connects the first surface to the second surface. The channel extends from a first channel opening of the first surface through the body to a second channel opening defined on the third surface. The channel has a channel axis extending through the first channel opening and the second channel opening. The channel axis intersects a first plane defined by the first channel opening at an angle transverse to the first plane. The channel is configured to receive a bone engagement member to attach the body to a shoulder bone. The at least one alignment member extends from the first surface to align the body to the shoulder bone. The bone engagement member can attach the body to the shoulder bone. The bone engagement member can occupy at least a portion of the channel.

In some embodiments, the at least one alignment member includes a first alignment member. The first alignment member defines a first alignment axis and a second alignment member defines a second alignment axis. The first alignment axis and second alignment axis define a second plane perpendicular to the first plane. The channel axis intersects the second plane between the first alignment axis and the second alignment axis. The glenoid component In some embodiments, the third surface defines a first, maximum diameter. The third surface can define a second diameter that is perpendicular to and bisects the first diameter. The second channel opening can be closer to the second diameter than the first diameter.

In some embodiments, a width of the third surface adjacent to the second channel opening can be greater than a width of the third surface on an opposite side of the third surface from the second channel opening.

In some embodiments, the third surface defines a first tangent line tangent to the third surface adjacent to the second channel opening and a second tangent line tangent to the third surface on an opposite side of the third surface from the second channel opening. A first angle defined between a second plane perpendicular to the first tangent line and the first surface where the third surface meets the first surface is greater than or equal to 5 degrees and less than or equal to 45 degrees or a second angle defined between a third plane perpendicular to the second tangent line and the first surface where the third plane meets the first surface is greater than or equal to 5 degrees and less than or equal to 45 degrees.

In some embodiments, the body defines a bisecting plane that bisects the body and is perpendicular to the first surface. The at least one alignment member can be on an opposite side of the bisecting plane from the second channel opening.

In some embodiments, the second surface is free of openings. The bone engagement member can be received posteriorly to anteriorly by the channel. The at least one alignment member can be integral with the body. The first surface can be textured.

According to another aspect of the present disclosure, a total shoulder arthroplasty system includes a body. The body includes a first surface that has a convex shape. The body includes a second surface opposite the first surface. The second surface has a concave shape. The system includes a third surface connecting the first surface to the second surface. The system includes a channel extending from a first channel opening of the first surface through the body to a second channel opening defined on the third surface. The channel has a channel axis extending through the first channel opening and the second channel opening. The channel axis intersects a first plane defined by the first channel opening at an angle transverse to the first plane. The channel is configured to receive a bone engagement member to attach the body to a shoulder bone. The at least one alignment member extends from the first surface to align the body to the shoulder bone. The system includes a bone engagement member to attach the body to the shoulder bone. The bone engagement member occupies at least a portion of the channel.

Some or all of the systems, components, and subcomponents of the present disclosure can be single-use or disposable. Also some or all of the systems, components, and subcomponents of the present disclosure can be made of a unitary construction (formed from a single piece of metal, plastic, or other material) or unitary modular construction (plurality of components and/or subcomponents permanently connected by standard means, such as welding or soldering), or of modular construction (plurality of components and/or subcomponents removably connected by standard means, such as threading or snap-fitting).

These and other features of various embodiments can be understood from a review of the following detailed description in conjunction with the accompanying drawings.

It is to be understood that both the foregoing general description and the following detailed description are explanatory and are not restrictive of the present disclosure, as claimed.

DETAILED DESCRIPTION

The following detailed description and the appended drawings describe and illustrate various glenoid component systems and methods. The description and drawings are provided to enable one of skill in the art to make and use one or more glenoid component systems and/or practice one or more methods. They are not intended to limit the scope of the claims in any manner.

The use of "e.g." "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "attached" and "coupled" and grammatically related terms refers to the fixed, releasable, or integrated association of two or more elements and/or devices with or without one or more other elements in between. Thus, the term "attached" or "coupled" and grammatically related terms include releasably attaching or fixedly attaching two or more elements and/or devices in the presence or absence of one or more other elements in between. As used herein, the terms "proximal" and "distal" are used to describe opposing axial ends of the particular elements or features being described in relation to anatomical placement.

In existing solutions, shoulder replacement devices may fail to stop or even exacerbate posterior bone erosion, resulting in the overall ineffectiveness or reduced lifetime of the shoulder replacement device. Although bone grafts may be used to address the problem of bone loss, posterior bone erosion can occur even after a total shoulder arthroplasty (TSA), which may cause additional problems and reduce the effectiveness of the TSA procedure. The present solution provides component systems and methods for improving shoulder prosthesis by using an all-metal glenoid component. The glenoid component includes a body, a first surface, a second surface, a third surface, a channel, and at least one alignment member. The first surface has a convex shape. The second surface has a concave shape and is opposite the first surface. The third surface connects the first surface to the second surface. The channel extends from a first channel opening of the first surface through the body to a second channel opening defined on the third surface. The channel has a channel axis extending through the first channel opening and the second channel opening. The channel axis intersects a first plane defined by the first channel opening at an angle transverse to the first plane. The channel is configured to receive a bone engagement member to attach the body to a shoulder bone. The at least one alignment member extends from the first surface to align the body to the shoulder bone.

Figure 1:
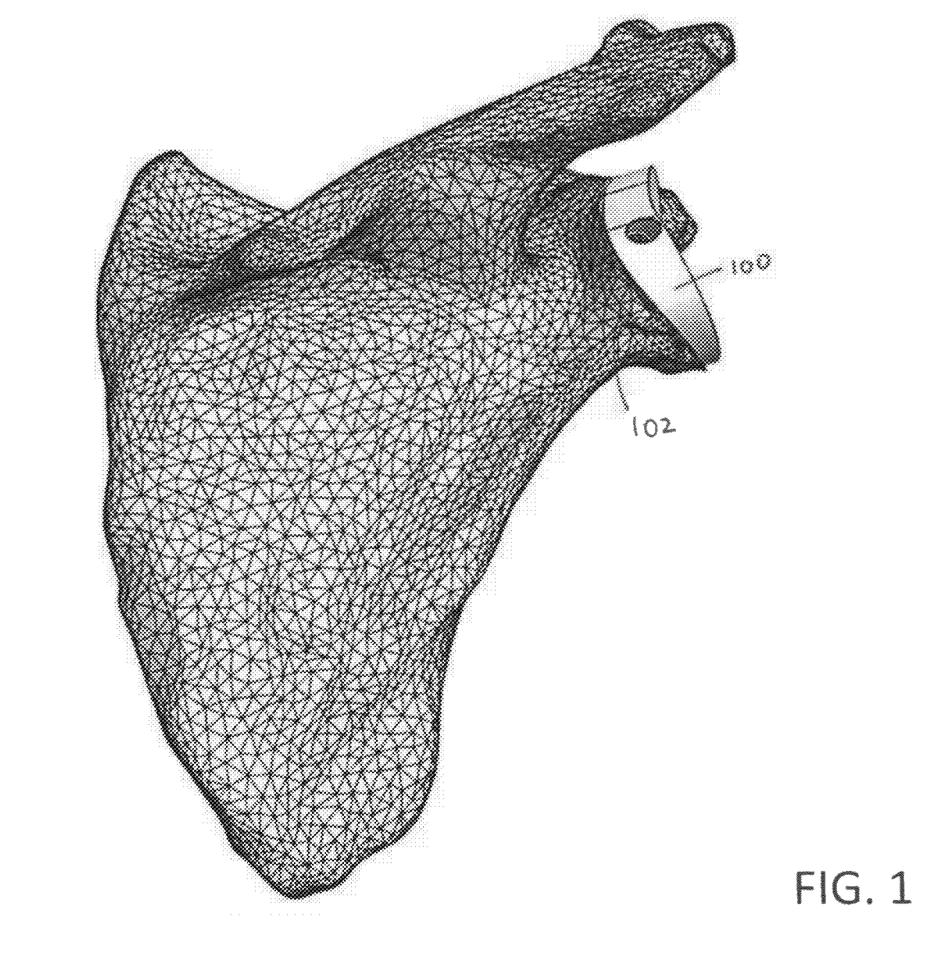
FIG. 1 is a perspective view of an embodiment of a glenoid component fixed to a portion of a shoulder bone.

Referring to FIG. 1, a perspective view of a shoulder prosthesis including a glenoid component 100 fixed to a portion 102 of a shoulder bone is shown. In some embodiments, the shoulder bone is a scapula. The glenoid component 100 can be oriented and secured (e.g. fixed, attached, etc.) to the portion 102 of the shoulder bone. In some embodiments, securing the glenoid component to the portion 102 of the shoulder bone reduces stress on the portion 102 of the shoulder bone to mitigate glenoid bone loss or posterior bone erosion. The portion 102 of the shoulder bone can be manipulated or altered through mechanical reaming. In some embodiments, the glenoid component 100 is an all-metal component. In some embodiments, the glenoid component 100 is inset into the portion 102 of the shoulder bone.

In some embodiments, the glenoid component 100 acts a socket in a ball-and-socket joint between a humeral head component (not shown) coupled to a humerus and the shoulder bone. The present solution can improve the effectiveness of a shoulder prosthesis for a patient, including relieving joint paint pain caused by shoulder arthritis and improving a range of motion of the shoulder joint.

In some embodiments, the glenoid component 100 is provided in a surgical kit. For example, the glenoid component 100 can be provided in a surgical kit that includes the humeral head component and a humeral stem component, such as a surgical kit used to perform total shoulder arthroplasty. The glenoid component 100 can be customized or otherwise designed to match a particular glenoid cavity or surgical reaming of a glenoid cavity. For example, the glenoid component 100 can be sized for a particular bone density or glenoid cavity dimensions.

In some embodiments, the glenoid component 100 is customized or otherwise designed for compatibility with a particular patient. For example, a model of the glenoid component 100 can be generated based on information regarding the shoulder of a patient, such as imaging data (e.g., Mill data, etc.). The information can indicate target location on the portion 102 for securing the glenoid component to the portion 102. For example, the information can include target can include target locations on a surface of the portion 102 through which a bone engagement member will be driven to secure the glenoid component 100 to the portion 102. The information can indicate locations on the portion 102 where bone loss has occurred or may occur, such as for avoiding these locations when securing the glenoid component 100 to the portion 102.

Figure 2:
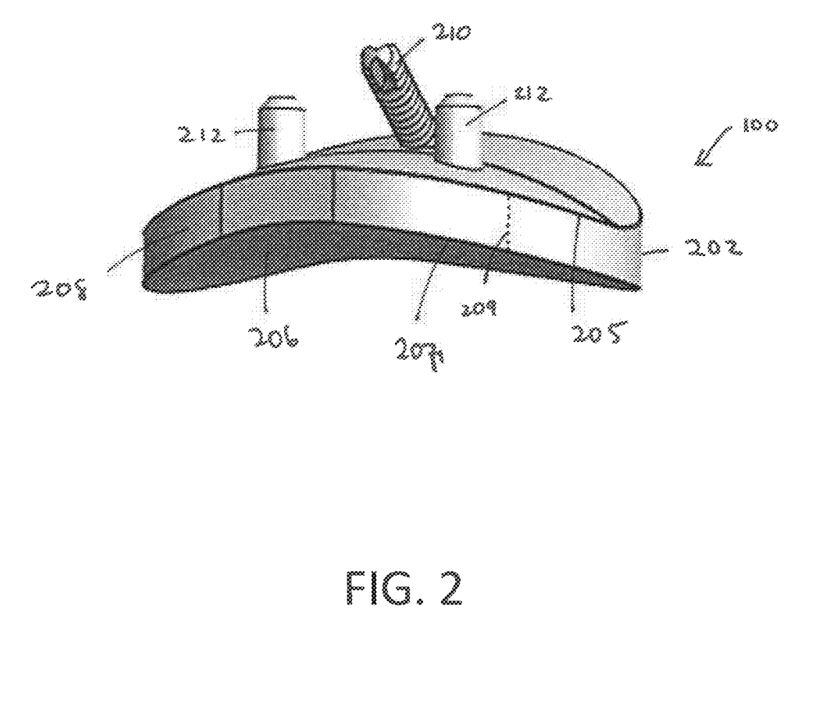
FIG. 2 is a perspective view of an embodiment of the glenoid component of FIG. 1.

Referring to FIG. 2, a perspective view of an embodiment of the glenoid component 100 is shown. The glenoid component includes a body 202. The body 202 can include a variety of shapes. For example, in various embodiments, the body 202 can include a substantially disk shape, a substantially bowl shape, or any other shape allowing the glenoid component 100 to act as part of a shoulder prosthesis. The body 202 can be made of metal, such as cobalt chrome or titanium. A body 202 made of metal can provide wear resistance against bone loss, such as posterior bone loss due to the humeral head wearing out the posterior part of the shoulder joint. In some embodiments, the body 202 is made of metal. For example, the body 202 can be made of an all-metal component.

The body 202 includes a first surface 204 that is convex. The convex shape of the first surface 204 allows the first surface to engage with the glenoid cavity or glenoid fossa of scapula. In some embodiments, the glenoid cavity can be surgically reamed to provide a contour-matching interface for the first surface 204 of the glenoid component 100. In some embodiments, the first surface 204 is made of a metal, such as titanium or cobalt chrome. The first surface can include a biocompatible roughened metal. The roughened metal can be applied onto the body 202, for example, through a grid-blasting process or plasma spray process, and can facilitate bony ingrowth onto the first surface 204 to improve fixation of the glenoid component 100 to the portion 102. The first surface 204 can have pores that facilitate bony ingrowth. In some embodiments, the first surface 204 can have a substantially oblong shape. The shape of the first surface 204 can conform to the shape of the glenoid cavity of the shoulder bone. The glenoid cavity of the shoulder bone can have a substantially oblong shape. The shape of the glenoid component 100 can be such that it fits into the glenoid cavity of the shoulder bone with minimal surgical invasiveness, which can include reaming of bone. The body 202, when formed using metal, can have improved fixation to the portion 102 relative to plastic components; for example, the body 202 can withstand greater biomechanical forces, as compared to plastic, which may slide on the portion 102 when receiving such forces.

The body 202 includes a second surface 206 that is concave. The second surface 206 is opposite the first surface 204. The concave shape of the second surface 206 allows the second surface 206 to engage other portions of a shoulder prosthesis system, such as a humeral head component (not shown). For example, the concave shape of the second surface 206 can provide the glenoid component 100 to act as a socket in a ball-and-socket prosthesis system such that the humeral head can articulate about the second surface 206. The second surface 206 has a substantially oblong shape. In some embodiments, the oblong shape of the second surface 206 can mimic a naturally occurring glenoid cavity found in a human shoulder bone. In some embodiments, the second surface 206 is an articulating surface about which a humeral head component or a glenosphere articulates. In some embodiments, the second surface 206 is made of a metal, such as cobalt chrome. In some embodiments, the second surface 206 is made of cobalt chrome to provide more scratch resistance than titanium would provide.

Figure 3:
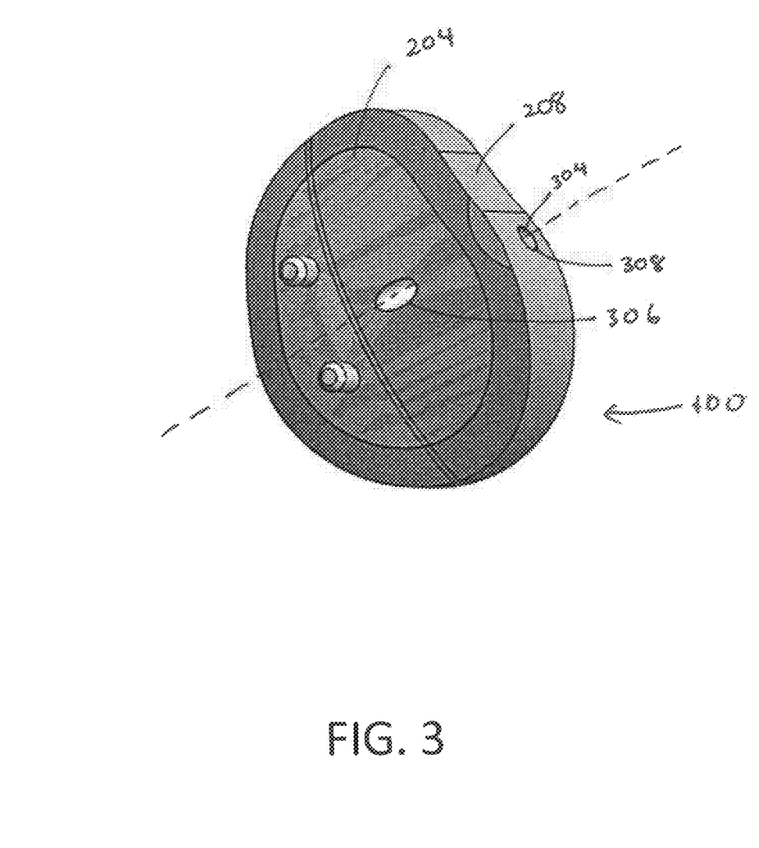
FIG. 3 is a perspective view of an embodiment of the glenoid component of FIG. 1.

In some embodiments, the second surface 206 is free of openings or does not define any openings. For example, the channel 304 as shown in FIG. 3 and described herein does not extend through the second surface 206. In some embodiments, any concavity of the second surface 206 does not extend through to the first surface 204. The second surface 206 being free of openings reduces the likelihood that particulate matter generated by friction the humeral head component and the body 202 can move into the glenoid cavity, or that particulate matter generated by friction between the body 202 and the glenoid cavity can move towards the humeral head.

The glenoid component 100 includes a third surface 208. The third surface 208 connects the first surface 204 to the second surface 206. In some embodiments, the third surface 208 can include a rim encircling a portion of the glenoid component. For example, the third surface 208 can connect an edge 205 of the first surface 204 to an edge 207 of the second surface 206. In some embodiments, the third surface 208 spaces the edge 205 of the first surface 204 from the edge 207 of the second surface 206 by a thickness 209 of the third surface 208. In some embodiments, the thickness 209 is a variable thickness. In some embodiments, the thickness is a constant thickness. The edge 205 of the first surface 204 can include a variety of shapes. For example, in various embodiments, the edge 205 can include a pencil shape, a bevel shape, a half bullnose, an ogee shape or any other shape that allows the first surface 204 to interface with the glenoid cavity. The edge 207 of the second surface 206 can include a variety of shapes. For example, in various embodiments, the edge 207 can include a square shape, a pencil shape, a bevel shape, a half bullnose, an ogee shape or any other shape that allows the first surface 207 to interface with a humeral head.

The glenoid component 100 can receive a bone engagement member 210. In some embodiments, the bone engagement member 210 attaches the glenoid component 100 to a shoulder bone. In some embodiments, the bone engagement member 210 can be located inside a channel 304 as shown in FIG. 3 and described herein. In some embodiments, the bone engagement member 210 can be configured to secure the glenoid component 100 to the portion 102 of the shoulder bone. The bone engagement member 210 can include engagement features (e.g., threads located on an outer surface of the bone engagement member 210) or other elements allowing the bone engagement member 210 to be driven through a surface of the portion 102 to be frictionally secured in the shoulder bone. In some embodiments, the bone engagement member 210 is made of metal. In some embodiments, the bone engagement member 210 does not pass through the second surface 206. The bone engagement member 210 can be a compression screw that engages with an angled surface, such as a chamfer, of the channel 304. The bone engagement member can be a locking screw having threads that engage with thread receiving features of the channel 304.

In some embodiments, the bone engagement member 210 enters the channel 304 posteriorly to anteriorly to prevent the humeral head from dislocating posteriorly. For example, posteriorly to anteriorly can include from the back side of the shoulder bone to the front side of the shoulder bone. In human subjects, the back side of the shoulder bone can be towards the dorsal side and the front side of the shoulder bone can be towards the ventral side. Posteriorly can include from the posterior or dorsal side. Anteriorly can include from the anterior or ventral side. In some embodiments, the bone engagement member 210 applies a force posteriorly to anteriorly to resist against posterior movement of the humeral head. In some embodiments, the bone engagement member 210 applies a force against the body 202 to secure the body 202 to the portion 102 of the shoulder bone. For example, the bone engagement member 210 can transmit a compressive force between the glenoid component 100 and the portion 102 of the shoulder bone.

In some embodiments, the bone engagement member 210 is situated in the channel 304. For example, the bone engagement member can be partially or completely within the channel 304. In some embodiments, the bone engagement member 210 can be restricted from exiting the channel 304 in one direction due to the shape of the channel 304 preventing the complete expulsion of the bone engagement member 210. In some embodiments, the bone engagement member 210 can only enter the channel 304 through the third surface 208. For example, the channel 304 can include a beveled section that prevents the bone engagement member 210 to pass completely through the channel 304. In some embodiments, the bone engagement member 210 extends past the alignment members 212 as described below.

The contact between the glenoid component 100 and the portion 102 of the shoulder bone can promote bone ingrowth or osseointegration. Contact between the glenoid component 100 and the portion 102 of the shoulder bone can include a fixed connection between the glenoid component 100 and the portion 102 of the shoulder bone. Bone ingrowth can include bone formation within an irregular surface of an implant, such as the glenoid component 100. Osseointegration can include a structural and functional connection between the surface of a load-carrying implant and a living bone. In some embodiments, osseointegration may result from a lack of negative tissue response coming from the portion 102 of the shoulder bone.

Figure 9:
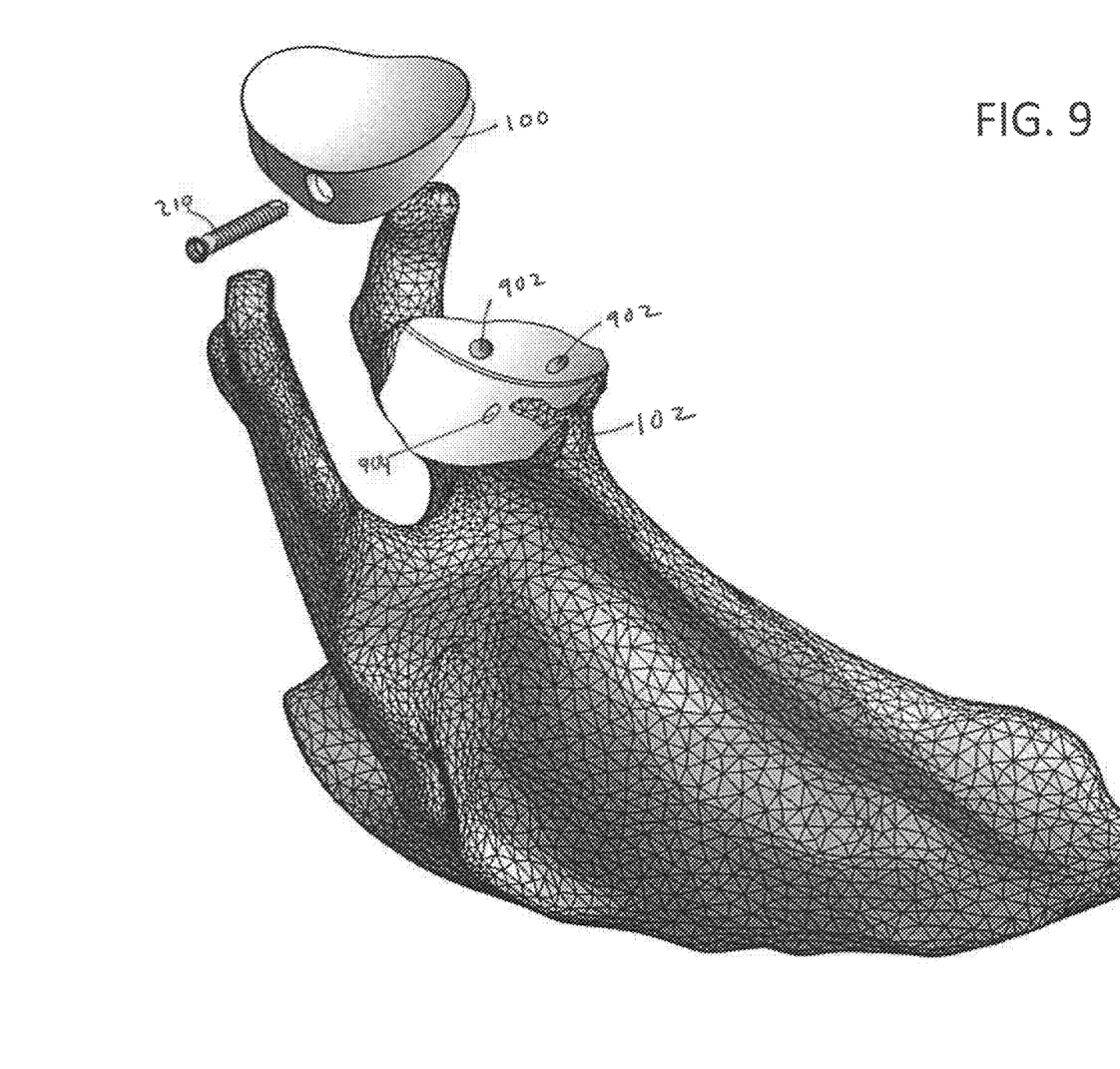
FIG. 9 is a perspective view of the glenoid component proximate to a reamed portion of shoulder bone.

The glenoid component 100 can include at least one alignment member 212. In some embodiments, the at least one alignment member 212 can extend from the first surface 204 to align the body 202 to the shoulder bone. The at least one alignment member 212 can include a variety of shapes. For example, in various embodiments, the at least one alignment member 212 can include a substantially peg shape, a substantially cylindrical shape, a substantially conical shape, or any other shape allowing the at least one alignment member 212 to insert into a cavity or hole. The at least one alignment member 212 can have flanges (e.g., at a distal end opposite the first surface 204). The at least one alignment member 212 can have threads to facilitate bony ingrowth. In some embodiments, the at least one alignment member 212 can have a length extending away from the first surface 204. The length may be five millimeters. The length may be greater than or equal to two millimeters and less than or equal to ten millimeters. The length may be greater than or equal to three millimeters and less than or equal to nine millimeters. The length may be greater than or equal to four millimeters and less than or equal to six millimeters. The at least one alignment member 212 can have a diameter. The diameter can be four millimeters. The diameter may be greater than or equal to two millimeters and less than or equal to ten millimeters. The diameter may be greater than or equal to three millimeters and less than or equal to nine millimeters. In some embodiments, the glenoid component 100 can include multiple alignment members 212 to align the body 202 to the shoulder bone. In some embodiments, the at least one alignment members 212 slot into alignment member cavities 902 in the shoulder bone as shown in FIG. 9 and described herein. In some embodiments, the at least one alignment member 212 can be driven into the portion 102 of the shoulder bone. The at least one alignment member 212 can be detached from the portion 102 of the shoulder bone through a transverse motion of the glenoid component.

In some embodiments, the at least one alignment member 212 is integral with the body 202 of the glenoid component 100. The at least one alignment member 212 can be located on the first surface 204 away from an edge 205 of the first surface 204. In some embodiments, the at least one alignment member 212 can extend away from the first surface 204. In some embodiments, the at least one alignment member 212 is located closer to the first channel opening 306 that to the second channel opening 308. In some embodiments, the at least one alignment member 212 can include two or more alignment members 212. For example, the at least one alignment member 212 can include exactly two alignment members 212. In some embodiments, the at least one alignment member 212 has a tapered head. For example, the top of the alignment member 212 can be a smaller width, thickness or diameter than the main body of the alignment member 212.

Referring to FIG. 3, a perspective view of an embodiment of the glenoid component is shown. In some embodiments, the glenoid component 100 includes a channel 304. The channel 304 can extend from a first channel opening 306 disposed on the first surface 204 through the body 202 to a second channel opening 308 disposed on the third surface 208. The channel 304 can extend from the third surface 208 through the body 202 to the first surface 204 enabling improved fixation of the glenoid component 100 while avoiding the creation of openings on the second surface 206. In this way, the second surface 206 can be free from any openings or voids on the second surface 206. The channel 304 can be configured to receive a bone engagement member 210. For example, the channel 304 can include engagement receiving features (e.g., slots, threads located on the surface of channel 304 extending from channel 304, etc.) configured to reciprocally engage engagement features of the bone engagement member 210. In some embodiments, the channel 304 is a constant width, thickness, or diameter. The channel 304 can be a variable width, thickness, or diameter.

In some embodiments, the first channel opening 306 is located on the second diameter 504. In some embodiments, the first channel opening 306 is located between the at least one alignment member 212. The first channel opening 306 can include a variety of shapes. For example, in various embodiments, the first channel opening 306 can include a substantially disk shape, a substantially ovular, or any other shape allowing a bone engagement member 210 to pass through the first channel opening 306.

Figure 5:
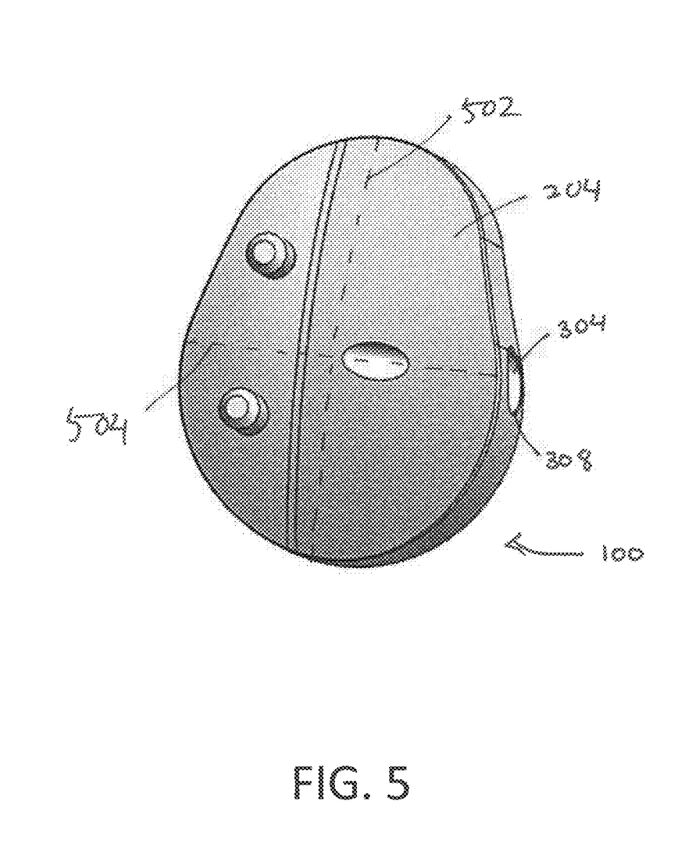
FIG. 5 is a side view of an embodiment of the glenoid component of FIG. 1.

In some embodiments, the second channel opening 308 is located on the first diameter 502 as shown in FIG. 5 and described herein. In some embodiments, the second channel opening 308 is located between the at least one alignment member 212. The second channel opening 308 can include a variety of shapes. For example, in various embodiments, the second channel opening 308 can include a substantially disk shape, a substantially ovular, or any other shape allowing a bone engagement member 210 to pass through the second channel opening 308.

Figure 8:
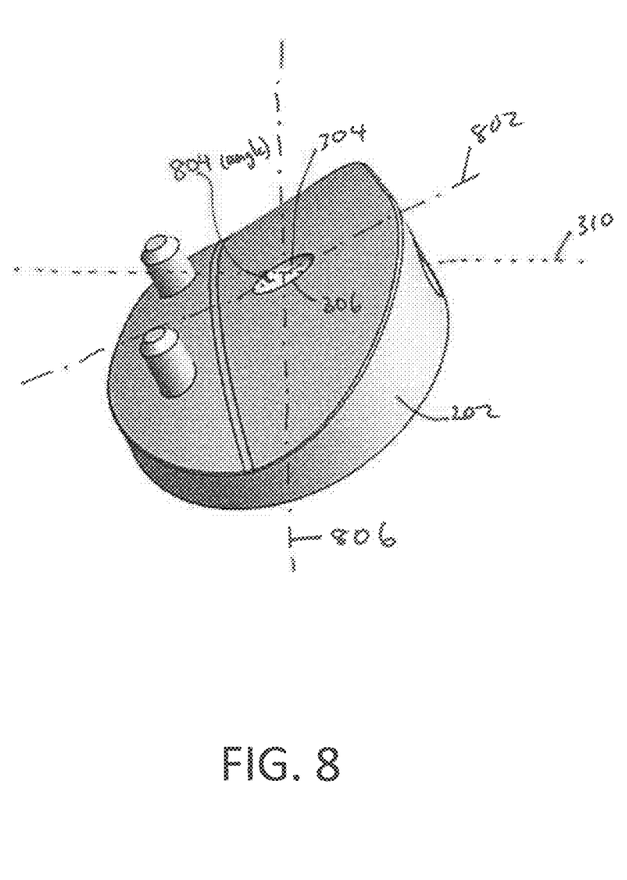
FIG. 8 is a side view of an embodiment of the glenoid component of FIG. 1.

The channel 304 can define a channel axis 310 passing through the body 202. The channel axis 310 can extend through the first channel opening 306 and the second channel opening 308. The channel axis 310 can intersect a first plane 802 as shown in FIG. 8 and described herein defined by the first channel opening 306 at an angle 804 transverse to the first plane 802. In some embodiments, the channel 304 is configured to receive a bone engagement member 210 to attach the glenoid component 100 to a shoulder bone. For example, the bone engagement member 210 can be received posteriorly-to-anteriorly, through the second channel opening 308 through the channel 304 and extending out of the first channel opening 306 to engage the portion 102 of the shoulder bone.

Figure 4:
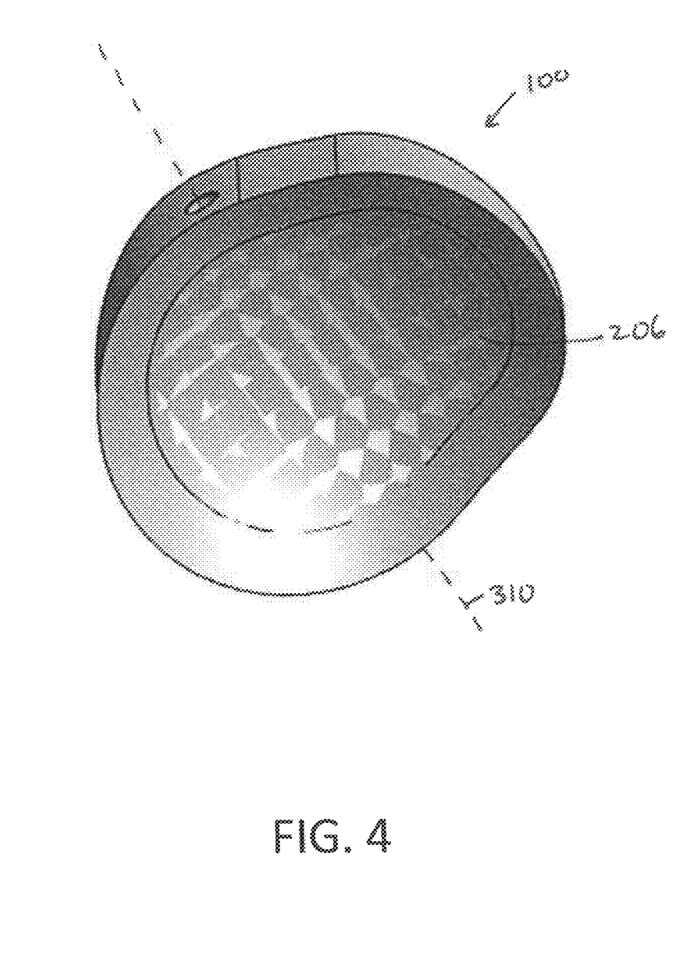
FIG. 4 is a side view of an embodiment of the glenoid component of FIG. 1.

Referring to FIG. 4, a side view of an embodiment of the glenoid component 100 is shown. The second surface 206 can be a surface with a low frictional coefficient to allow a humeral head (not shown) or a glenosphere (not shown) to easily articulate about the second surface 206. The second surface 206 can have a substantially concave shape. In some embodiments, the concave shape of the second surface 206 allows the second surface 206 to engage other portions of a shoulder prosthesis system, such as a humeral head component (not shown). For example, the concave shape of the second surface 206 can provide the glenoid component 100 to act as a socket in a ball-and-socket prosthesis system such that the humeral head can articulate about the second surface 206. The second surface 206 has a substantially oblong shape. In some embodiments, the oblong shape of the second surface 206 can mimic a naturally occurring glenoid cavity found in a human shoulder bone. In some embodiments, the second surface 206 is an articulating surface about which a humeral head component or a glenosphere articulates. In some embodiments, the second surface 206 is made of a metal, such as cobalt chrome.

In some embodiments, the second surface 206 is free of openings or does not define any openings. For example, the channel 304 does not extend through the second surface 206. The second surface 206 being free of openings reduces the likelihood that particulate matter generated by friction the humeral head component and the body 202 can move into the glenoid cavity, or that particulate matter generated by friction between the body 202 and the glenoid cavity can move towards the humeral head.

Referring to FIG. 5, a side view of an embodiment of the glenoid component 100 is shown. The first surface 204 can include frictional elements configured to frictionally engage the first surface 204 to the portion 102 of the shoulder bone to promote bone ingrowth. For example, the first surface 204 can include a textured surface that enhances frictional engagement between the first surface 204 and the portion 102 of the shoulder bone. A textured surface can include a surface with a high number of spaced surface irregularities or roughness. In some embodiments, the first surface 204 can have a substantially oblong shape. The shape of the first surface 204 can conform to the shape of the glenoid cavity of the shoulder bone. The glenoid cavity of the shoulder bone can have a substantially oblong shape. The shape of the glenoid component 100 can be such that it fits into the glenoid cavity of the shoulder bone with minimal surgical invasiveness, which can include reaming of bone.

In some embodiments, the third surface 208 defines a first, maximum diameter 502 and a second diameter 504 that is perpendicular to and bisects the first diameter 502. The first diameter 502 can be defined by the maximum distance between any two points on the third surface 208. In some embodiments, the second channel opening 308 is closer to the second diameter 504 than the first diameter 502. For example, the channel 304 can go from the third surface 208 through the body 202 to the first surface 204, rather than through the second surface 206, enabling improved fixation of the glenoid component 100 while avoiding the creation of openings on the second surface 206. In some embodiments, the at least one alignment member 212 can include two or more alignment members 212. For example, two alignment members 212 can be located on one side of the glenoid component 100 as demarcated by a line passing through the maximum diameter 502. In some embodiments, two alignment members 212 can be located on opposite sides of the glenoid component 100 as demarcated by a line passing through the minimum diameter 504.

Figure 6:
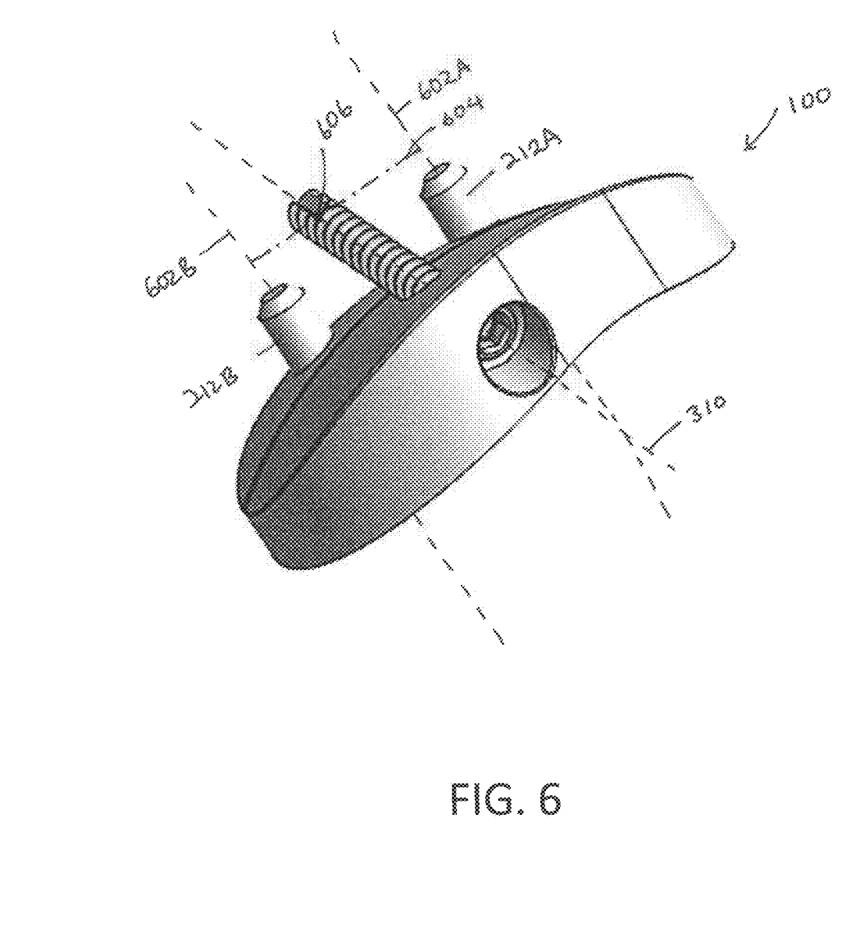
FIG. 6 is a side view of an embodiment of the glenoid component of FIG. 1 with a bone engagement member disposed within the channel.

Referring to FIG. 6, a side view of an embodiment of the glenoid component 100 with a bone engagement member 210 disposed within the channel 304 is shown. In some embodiments, the bone engagement member 210 can extend partially or completely through the channel 304. The bone engagement member 210 can intersect the first plane 802 as shown in FIG. 8 and described herein defined by the first channel opening 306.

The glenoid component 100 can include at least one alignment member 212 defining an alignment axis 602. In some embodiments, the glenoid component includes a first alignment member 212A defining a first alignment axis 602A and a second alignment member 212B defining a second alignment axis 602B. The first alignment axis 602A can intersect the first alignment member 212A at a single point. The second alignment axis 602B can intersect the second alignment member 212B at a single point. The first alignment axis 602A and the second alignment axis 602B can define a second plane 604 perpendicular to the first plane 802 as shown in FIG. 8 and described herein. The channel axis 310 can intersect the second plane at a point 606 between the first alignment axis 212A and the second alignment axis 212B. The orientation of the channel axis 310 can enable a bone engagement member 210 to be received in a posterior-to-anterior manner, thereby deterring the humeral head from dislocating posteriorly. The point 606 can be closer to the first alignment member 212A than to the second alignment member 212B. The point 606 can be closer to the second alignment member 212B than to the first alignment member 212A. The point 606 can be equidistant from the first alignment member 212A and the second alignment member 212B.

Figure 7:
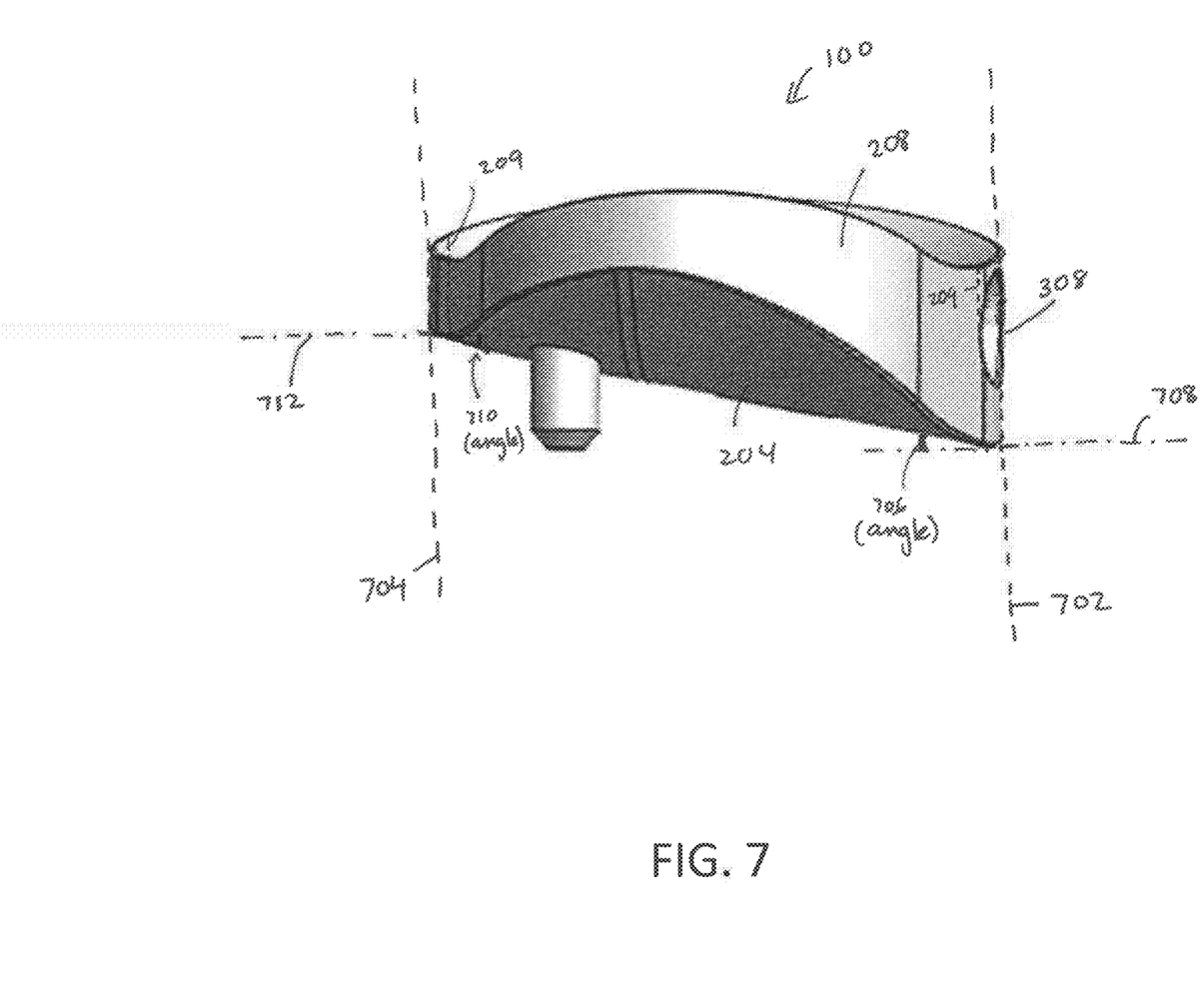
FIG. 7 is a side view of an embodiment of the glenoid component of FIG. 1.

Referring to FIG. 7, a side view of an embodiment of the glenoid component 100 is shown. In some embodiments, the third surface 208 is thicker near the second channel opening 308 than on an opposite side of the third surface 208. For example, a thickness 209 of the third surface 208 adjacent to the second channel opening 308 can be greater than a thickness 209 of the third surface 208 on an opposite side of the third surface 208 from the second channel opening 308, such as at a position on the third surface 208 diametrically opposed from the second channel opening 308.

In some embodiments, the third surface 208 defines a first tangent line 702 tangent to the third surface 208 adjacent to the second channel opening 308. The first tangent line 702 can be tangent or adjacent to the second channel opening 308. The third surface 208 can define a second tangent line 704 tangent to the third surface 208 on an opposite side of the third surface 208 from the second channel opening 308, such as at a position on the third surface 208 diametrically opposed from the second channel opening 308.

The body 202 of the glenoid component 100 can define a shape that allows the glenoid component 100 to contour with the shape of a glenoid cavity. The first angle 706 and second angle 708 described below can allow the channel 304 to extend from the first surface 204 to the third surface 208 without intersecting the second surface 206. The glenoid component 100 can define a first angle 706 between a second plane 708 perpendicular to the first tangent line 702 and the first surface 204 where the third surface 208 meets the first surface 204 (e.g., at where edge 205 of the third surface 208 meets the first tangent line 702) is greater than or equal to 5 degrees and less than or equal to 45 degrees. In some embodiments, a second angle 710 defined between a third plane 712 perpendicular to the second tangent line 704 and the first surface 204 where the third plane 712 meets the first surface 204 (e.g., at where edge 207 of the first third surface 208 meets the second tangent line 704) is greater than or equal to 5 degrees and less than or equal to 45 degrees. The first angle 706 can be less than, equal to, or greater than the second angle 708. In some embodiments, the first angle 706 and the second angle 710 can be selected to match the contours of the glenoid cavity. In some embodiments, the first angle 706 and the second angle 710 can be selected to allow the channel 304 to pass through the body 202 of the glenoid component 100 without the channel 304 passing through the second surface 206. In some embodiments, first surface 204 at the point where the second angle 710 is defined slopes faster than at the point where the first angle 706 is defined. In some embodiments, first surface 204 at the point where the first angle 706 is defined has a smaller gradient than at the point where the second angle 710 is defined. In some embodiments, first surface 204 at the point where the first angle 706 is defined has a smaller slope than at the point where the second angle 710 is defined. In some embodiments, first surface 204 at the point where the second angle 710 is defined has a larger gradient than at the point where the first angle 706 is defined.

In some embodiments, the second plane 708 and the third plane 712 are parallel or intersect one another. In some embodiments, the second plane 708 is tangent to the first surface 204. In some embodiments, the second plane 708 does not intersect the body 202 of the glenoid component 100. In some embodiments, the second plane 708 intersects the channel axis 310. In some embodiments, the third plane 712 is tangent to the third surface 208. In some embodiments, the third plane 712 intersects the body 202 of the glenoid component 100. In some embodiments, the third plane 712 intersects the channel axis 310.

Referring to FIG. 8, a side view of an embodiment of the glenoid component 100 is shown. The channel 304 can define a channel axis 310 passing through the body 202. The channel axis 310 can extend through the first channel opening 306 and the second channel opening 308. The channel axis 310 can intersect a first plane 802 as shown in FIG. 8 and described herein defined by the first channel opening 306 at an angle 804 transverse to the first plane 802. The channel axis 310 can intersect the first plane 802 at an angle 804 greater than 0 degrees and less than 90 degrees. The angle 804 can be transverse to the first plane 802 such that the channel axis 310 is not perpendicular to the first surface 204. The plane 802 can divide the body 202 into two substantially equal or congruent parts.

In some embodiments, the body 202 defines a bisecting plane 806 that bisects the body 202 and is perpendicular to the first surface 204. The at least one alignment member 212 can be on an opposite side of the bisecting plane 806 from the second channel opening 308. In some embodiments, the body 202 defines a bisecting plane 806 that is substantially bisecting. For example, the bisecting plane 806 can divide the body 202 into two substantially equal or congruent parts.

Referring to FIG. 9, a perspective view of the glenoid component proximate to a reamed portion 102 of shoulder bone is shown. In some embodiments, the portion 102 of the shoulder bone can include an alignment member cavity 902. The alignment member cavity 902 can include a variety of shapes. For example, in various embodiments, the alignment member cavity 902 can include a substantially cylindrical shape, a substantially rod shape, or any other shape allowing the alignment member 212 to slot into the alignment member cavity 908. The alignment member cavity 902 can be surgically created to allow the glenoid component 100 to align itself with the glenoid cavity. In some embodiments, the portion 102 of the shoulder bone can include a plurality of alignment member cavities 902.

In some embodiments, the portion 102 of the shoulder bone can include a bone engagement cavity 904. The bone engagement cavity 904 can include a variety of shapes. For example, in various embodiments, the bone engagement cavity 904 can include a substantially cylindrical shape, a substantially rod shape, or any other shape allowing the bone engagement member 210 to slot into the bone engagement cavity 904. The bone engagement cavity 904 can be surgically created to allow the glenoid component 100 to affix or attach to a portion 102 of the shoulder bone. In some embodiments, the portion 102 of the shoulder bone can include a plurality of bone engagement cavities 904.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

What is claimed is:

1. A glenoid component for use in a shoulder prosthesis, comprising:
   a body including a first surface that is convex and a second surface opposite the first surface, the second surface is concave and free of openings;
   a third surface connecting the first surface to the second surface;
   a channel extending from a first channel opening of the first surface through the body to a second channel opening defined on the third surface, the channel having a channel axis extending through the first channel opening and the second channel opening, the channel axis intersecting a first plane defined by the first channel opening at an angle transverse to the first plane, the channel configured to receive a bone engagement member to attach the body to a shoulder bone;

at least one alignment member extending from the first surface to align the body to the shoulder bone; and a bone engagement member to attach the body to the shoulder bone, the bone engagement member to occupy at least a portion of the channel.

2. The component of claim 1, wherein:
the third surface defines a first tangent line tangent to the third surface adjacent to the second channel opening and a second tangent line tangent to the third surface on an opposite side of the third surface from the second channel opening; and
at least one of (i) a first angle defined between a second plane perpendicular to the first tangent line and the first surface where the third surface meets the first surface is greater than or equal to 5 degrees and less than or equal to 45 degrees; or (ii) a second angle defined between a third plane perpendicular to the second tangent line and the first surface where the third plane meets the first surface is greater than or equal to 5 degrees and less than or equal to 45 degrees.

3. The component of claim 1, wherein:
the third surface defines a first, maximum diameter, and a second diameter that is perpendicular to and bisects the first diameter; and
the second channel opening is closer to the second diameter than the first diameter.

4. The component of claim 1, wherein:
a width of the third surface adjacent to the second channel opening is greater than a width of the third surface on an opposite side of the third surface from the second channel opening.

5. The component of claim 1, wherein:
the at least one alignment member includes a first alignment member defining a first alignment axis and a second alignment member defining a second alignment axis, the first alignment axis and second alignment axis define a second plane perpendicular to the first plane, and the channel axis intersects the second plane between the first alignment axis and the second alignment axis.

6. The component of claim 1, wherein:
the body defines a bisecting plane that bisects the body and is perpendicular to the first surface; and
the at least one alignment member is on an opposite side of the bisecting plane from the second channel opening.

7. The component of claim 1, wherein the bone engagement member is received posteriorly to anteriorly by the channel.

8. The component of claim 1, wherein the at least one alignment member is integral with the body.

9. The component of claim 1, wherein the first surface is textured.

10. A total shoulder arthroplasty system, comprising:
a body including a first surface that is convex and a second surface opposite the first surface, the second surface is concave and free of openings;
a third surface connecting the first surface to the second surface;
a channel extending from a first channel opening of the first surface through the body to a second channel opening defined on the third surface, the channel having a channel axis extending through the first channel opening and the second channel opening, the channel axis intersecting a first plane defined by the first channel opening at an angle transverse to the first plane, the channel configured to receive a bone engagement member to attach the body to a shoulder bone;

at least one alignment member extending from the first surface to align the body to the shoulder bone; and a bone engagement member to attach the body to the shoulder bone, the bone engagement member to occupy at least a portion of the channel.

11. The total shoulder arthroplasty system of claim 10, wherein:
the third surface defines a first tangent line tangent to the third surface adjacent to the second channel opening and a second tangent line tangent to the third surface on an opposite side of the third surface from the second channel opening; and
at least one of (i) a first angle defined between a second plane perpendicular to the first tangent line and the first surface where the third surface meets the first surface is greater than or equal to 5 degrees and less than or equal to 45 degrees; or (ii) a second angle defined between a third plane perpendicular to the second tangent line and the first surface where the third plane meets the first surface is greater than or equal to 5 degrees and less than or equal to 45 degrees.

12. The total shoulder arthroplasty system of claim 10, wherein:
the third surface defines a first, maximum diameter, and a second diameter that is perpendicular to and bisects the first diameter; and
the second channel opening is closer to the second diameter than the first diameter.

13. The total shoulder arthroplasty system of claim 10, wherein:
a width of the third surface adjacent to the second channel opening is greater than a width of the third surface on an opposite side of the third surface from the second channel opening.

14. The total shoulder arthroplasty system of claim 10, wherein:
the at least one alignment member includes a first alignment member defining a first alignment axis and a second alignment member defining a second alignment axis, the first alignment axis and second alignment axis define a second plane perpendicular to the first plane, and the channel axis intersects the second plane between the first alignment axis and the second alignment axis.

15. The total shoulder arthroplasty system of claim 10, wherein:
the body defines a bisecting plane that bisects the body and is perpendicular to the first surface; and
the at least one alignment member is on an opposite side of the bisecting plane from the second channel opening.

16. The total shoulder arthroplasty system of claim 10, wherein the bone engagement member is received posteriorly to anteriorly by the channel.

17. The total shoulder arthroplasty system of claim 10, wherein the at least one alignment member is integral with the body.

18. The total shoulder arthroplasty system of claim 10, wherein the first surface is textured.

19. A glenoid component for use in a shoulder prosthesis, comprising:

a body including a first surface that is convex and a second surface opposite the first surface, the second surface is concave;

a third surface connecting the first surface to the second surface;

a channel extending from a first channel opening of the first surface through the body to a second channel opening defined on the third surface, the channel having a channel axis extending through the first channel opening and the second channel opening, the channel axis intersecting a first plane defined by the first channel opening at an angle transverse to the first plane, the channel configured to receive a bone engagement member to attach the body to a shoulder bone;

at least one alignment member extending from the first surface to align the body to the shoulder bone; and a bone engagement member to attach the body to the shoulder bone, the bone engagement member to occupy at least a portion of the channel, wherein the third surface defines a first tangent line tangent to the third surface adjacent to the second channel opening and a second tangent line tangent to the third surface on an opposite side of the third surface from the second channel opening; and wherein at least one of (i) a first angle defined between a second plane perpendicular to the first tangent line and the first surface where the third surface meets the first surface is greater than or equal to 5 degrees and less than or equal to 45 degrees; or (ii) a second angle defined between a third plane perpendicular to the second tangent line and the first surface where the third plane meets the first surface is greater than or equal to 5 degrees and less than or equal to 45 degrees.

* * * * *